(12) United States Patent
Miller et al.

(10) Patent No.: US 9,187,449 B2
(45) Date of Patent: Nov. 17, 2015

(54) COMPOUNDS WITH INCREASED SPECIFICITY FOR THE TREATMENT OF GLIOMA

(71) Applicant: University of Tennessee Research Foundation, Memphis, TN (US)

(72) Inventors: Duane D. Miller, Collierville, TN (US); Shivaputra Appanna Patil, Germantown, TN (US); Renukadevi Patil, Germantown, TN (US); Terreia Jones, Denver, CO (US); Amira Ahmed, Memphis, TN (US); Likeselam Asres, Memphis, TN (US); Charles Ryan Yates, Collierville, TN (US); Eldon Geisert, Germantown, TN (US)

(73) Assignee: The University of Tennessee Research Foundation, Memphis, TN (US)

( * ) Notice: Subject to any disclaimer, the term of this patent is extended or adjusted under 35 U.S.C. 154(b) by 0 days.

(21) Appl. No.: 14/224,743

(22) Filed: Mar. 25, 2014

(65) Prior Publication Data

US 2014/0296286 A1 Oct. 2, 2014

Related U.S. Application Data

(60) Provisional application No. 61/806,783, filed on Mar. 29, 2013.

(51) Int. Cl.
*C07D 401/10* (2006.01)
*A61K 31/47* (2006.01)

(52) U.S. Cl.
CPC .................................. *C07D 401/10* (2013.01)

(58) Field of Classification Search
None
See application file for complete search history.

(56) References Cited

U.S. PATENT DOCUMENTS

| | | | |
|---|---|---|---|
| 6,593,322 B1 * | 7/2003 | Bhagwat et al. | 514/213.01 |
| 2007/0270460 A1 | 11/2007 | Miller et al. | |
| 2008/0146597 A1 | 6/2008 | Patil et al. | |
| 2009/0192188 A1 | 7/2009 | Liu | |

OTHER PUBLICATIONS

ISR and Written Opinion of the corresponding PCT/US2014/31754, (Aug. 2014).
PUBCHEM SureCN12090266, CID 15271090, pp. 1-3, Create Date: Feb. 10, 2007.

* cited by examiner

*Primary Examiner* — Zinna Northington Davis
(74) *Attorney, Agent, or Firm* — Lihua Zheng (57) ABSTRACT

Disclosed are compounds for the treatment of cancer. Compounds disclosed herein are particularly effective for the selective inhibition of glioma cells.

8 Claims, 6 Drawing Sheets

COMPOUNDS WITH INCREASED SPECIFICITY FOR THE TREATMENT OF GLIOMA

CROSS REFERENCE TO RELATED APPLICATIONS

This application claims the benefit of U.S. Provisional Application 61/806,783, filed on Mar. 29, 2013, which is incorporated herein by reference.

FIELD OF INVENTION

The invention relates to compounds which may be categorized as chemotherapeutic agents. More specifically, the invention relates to compounds categorized as tetrahydroisoquinoline derivatives which may be useful as chemotherapeutic agents for cancer treatment.

BACKGROUND

Significant progress has been made in the treatment of certain cancers, and the prognosis for individuals with some types of cancers, such as prostate, breast, thyroid, and skin cancer (i.e., certain melanomas) is generally good for at least 4 out of 5 patients. According to the United States National Institutes of Health, however, the prognosis for individuals with cancers such as those of the brain (27.3% survival), lung (13.4% survival), liver (6.0% survival), and pancreas (3.2% survival) has been poor, based upon statistics compiled from 1983 to 1990. According to the American Cancer Society, almost 22,000 people in the United States alone develop brain and nervous system cancers each year, and about 13,070 people die from these cancers. About 42 percent of all brain tumors are gliomas. Grade IV astrocytoma (glioblastoma multiforme, or GBM), for example, is considered by many to be the most malignant brain tumor. The average length of survival for people with GBM is 12 to 14 months, and common symptoms of GBM are seizures, nausea and vomiting, headaches that become progressively worse, a declining ability to move certain parts of the body, and weakness or numbness in the face or arm. GBM rapidly affects the quality of the patient's life, and it may affect individuals of any age.

Discovering and developing effective therapeutic agents for difficult-to-treat cancers is important both for the benefit of individuals who are diagnosed with those cancers, as well as for individuals who may have other difficult-to-treat forms of cancer. For example, researchers at the University of Minnesota's Masonic Cancer Center have discovered a genetic link between two types of cancers for which effective treatment has been achieved in only a small fraction of the individuals diagnosed with those cancers—glioblastoma and leukemia. Agents that are found to effectively treat one form of these difficult cancers may therefore provide excellent lead compounds for testing as therapeutic agents for other cancers which are known to be more refractory to treatment. What are needed are agents that effectively treat cancers and provide increased life expectancy and quality of life for thousands of individuals who are diagnosed with cancer each year.

BRIEF SUMMARY OF THE INVENTION

In one aspect, the invention relates to compounds of Formula I wherein $R^1$, $R^2$, $R^3$, and $R^4$ are each independently H, OH, or $OCH_3$;
$R^5$ is H, HCl, $CH_3$, or $COOC(CH_3)_3$;
X is C or N,
$R^6$ is H or HCl; and
$R_7$ is H or $OCH_3$.

In various aspects, compounds of the invention may be represented by Formula (I), wherein R1 and R4 are H and R2 and R3 are OH, X is C, R6 is H, and R7 is H.

In various aspects, when any two of R1, R2, R3, and R4 are —OCH3 and the remaining two of R1, R2, R3, and R4 are H, X is N, R6 is HCl, and R7 is OCH3.

In other aspects, the invention also provides methods for administering compounds of Formula I for inhibiting the growth of glioma cells.

BRIEF DESCRIPTION OF THE DRAWINGS

FIG. 1 illustrates synthesis scheme 1 for synthesizing compounds which were previously described by the inventors. These reactions may be utilized to produce some of the desired modifications to produce compounds of the present invention. Reagents and conditions: a. (EtO)2P(O)CN, Et3N, DMF, 0 0 C to RT; b. POCl3, CH3CN, Reflux 6 h; c. NaBH4, MeOH, RT, overnight; d. 1N NaOH, DCM, RT, 2 h; e. [(CH3)2C.CO2]2O, 1N NaOH, THF, RT, overnight; f. 4-methoxypyridin-3-yl-boronic acid, Pd2(dba)3,2-(dicyclohexylphosphino)-2',4',6'-tri-i-propyl-1,1'-biphenyl, k3PO4, i-PrOH, Reflux, 16 h; g. CF3COOH, DCM, 0 0 C to RT, 2 h; h. 37% HCl, 1N NaOH, 2M HCl in Ether, 0 0 C to RT, overnight.

FIG. 2 illustrates synthesis scheme 2 for synthesizing compounds of the invention, such as compound 12. Reagents and conditions: a. (EtO)2P(O)CN, Et3N, DMF, 0 0 C to RT; b. POCl3, CH3CN, Reflux 6 h; c. NaBH4, MeOH, RT, overnight; d. 1N NaOH, DCM, RT, 2 h; e. [(CH3)2C.CO2]2O, 1N NaOH, THF, RT, overnight; f. 4-methoxypyridin-3-yl-boronic acid, Pd2(dba)3,2-(dicyclohexylphosphino)-2',4',6'-tri-i-propyl-1,1'-biphenyl, k3PO4, i-PrOH, Reflux, 16 h; g. CF3COOH, DCM, 0 0 C to RT, 2 h; h. 37% HCl, 1N NaOH, 2M HCl in Ether, 0 0 C to RT, overnight.

DETAILED DESCRIPTION OF THE INVENTION

The inventors have previously described compounds comprising tetrahydroisoquinoline compounds that have demonstrated varying effectiveness in inhibiting and/or killing glioma cells. These compounds display significant specificity for the cancer cells, generally sparing non-cancerous cells to a certain extent at effective concentrations. See, e.g., U.S. Pat. No. 8,507,523, which is incorporated by reference in its entirety. However, the inventors have made it their goal to produce therapeutic compounds for cancer treatment that are even more effective and cancer cell-specific. Disclosed herein are compounds exhibiting significant effectiveness and specificity for inhibiting and killing cancer cells, including, for example, glioma cells.

In one aspect, the inventors have synthesized compositions with selective cytotoxicity for cancer cells. Compositions described by the present invention include compounds as in Formula (I):

wherein $R^1$, $R^2$, $R^3$, and $R^4$ are each independently H, OH, or $OCH_3$;
$R^5$ is H, HCl, $CH_3$, or $COOC(CH_3)_3$;
X is C or N,
$R^6$ is H or HCl; and
$R_7$ is H or $OCH_3$.

In some embodiments of compounds represented by Formula (I), R1 and R4 are H and R2 and R3 are OH, X is C, R6 is H, and R7 is H.

In other embodiments of the compounds represented by Formula (I), when any two of R1, R2, R3, and R4 are —OCH3 and the remaining two of R1, R2, R3, and R4 are H, X is N, R6 is HCl, and R7 is OCH3.

Compounds of the present invention may be synthesized using methods described herein, as well as methods for forming the tetrahydroisoquinoline and biphenyl moieties of the compounds which have been described previously in U.S. Pat. Nos. 7,241,774 and 7,718,672.

In other embodiments, compositions of the invention are provided for the treatment of a variety of forms of cancer in human and animals. For example, compounds of the invention are highly effective for the treatment of glioma, retinoblastoma, and other forms of cancer.

Therapeutically effective amounts of the inventive compositions may vary among individuals, depending upon the type of cancer, the body mass of the individual, the age of the individual, etc., as do all pharmaceutical compositions. Assessment of a therapeutically effective amount is well within the skill of one in the medical and pharmaceutical arts, given the disclosure herein. For example, the U.S. Department of Health and Human Services Food and Drug Administration Center for Drug Evaluation and Research (CDER) has established guidance for estimating dosages (*Guidance for Industry: Estimating the Maximum Safe Starting Dose in Initial Clinical Trials for Therapeutics in Adult Healthy Volunteers*, July 2005).

Useful dosages of the compounds of formula I for human and/or animal use can be determined by comparing their in vitro and in vivo activities in animal models. Methods for the extrapolation of effective dosages for humans, based on results from mice and other animals, are known to those of skill in the art and are described in various written references, such as, for example, U.S. Pat. No. 4,938,949.

Compositions of the present invention may also include pharmacologically acceptable salts thereof. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts may be obtained using standard procedures well known in the art such as, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds of formula (I) may be formulated as pharmaceutical compositions that may be administered to a mammalian subject such as a human patient via a variety of forms adapted to the chosen route(s) of administration, such as by oral, parenteral, intravenous, intramuscular, topical or subcutaneous routes. The present compounds may be systemically or orally administered, for example, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compound may also be administered intravenously or intraperitoneally by infusion or injection. Solutions of the compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations may contain a preservative to prevent the growth of microorganisms.

The pharmaceutical dosage forms suitable for injection or infusion may include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms may be achieved by various antibacterial and antifungal agents, for example, parabens, chlorobutanol, phenol, sorbic acid, thiomersal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions may be prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the present compounds may be applied in pure form, e.g., when they are liquids. However, it may generally be desirable to administer them to the skin as compositions or formulations, in combination with a dermatologically acceptable carrier, which may be a solid or a liquid. Useful solid carriers may include, for example, finely divided solids such as talc, clay, microcrystalline cellulose, silica, and alumina. Useful liquid carriers may include, for example, water, dimethyl sulfoxide (DMSO), alcohols or glycols or water-alcohol/glycol blends, in which the present compounds can be dissolved or dispersed at effective levels, optionally with the aid of non-toxic surfactant. Thickeners such as synthetic polymers, fatty acids, fatty acid salts and esters, fatty alcohols, modified celluloses or modified mineral materials may also be employed with liquid carriers to form, for example, spreadable pastes, gels, ointments, or soaps for application directly to the skin of the user.

EXAMPLES

Figure 1:
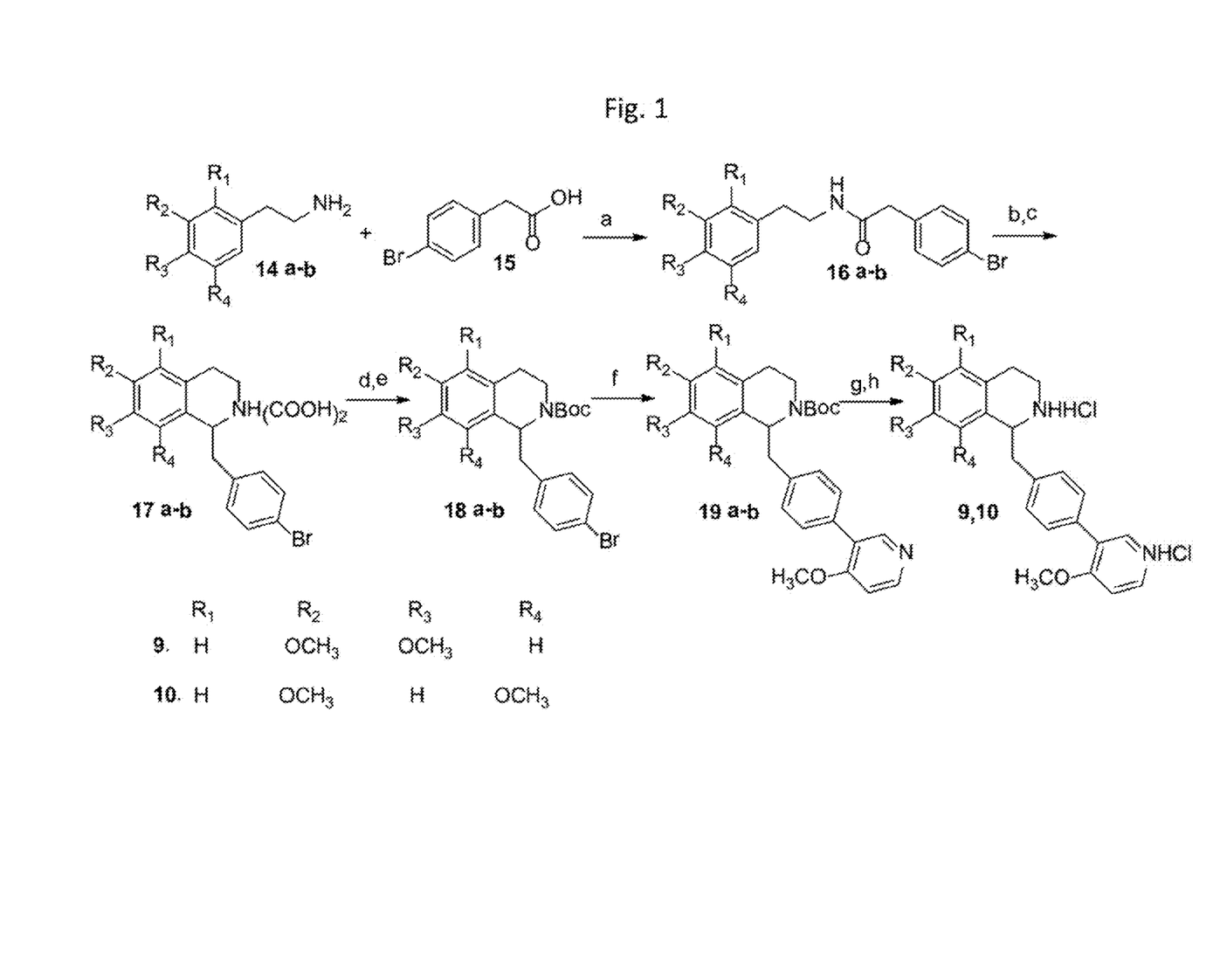
Figure 2:
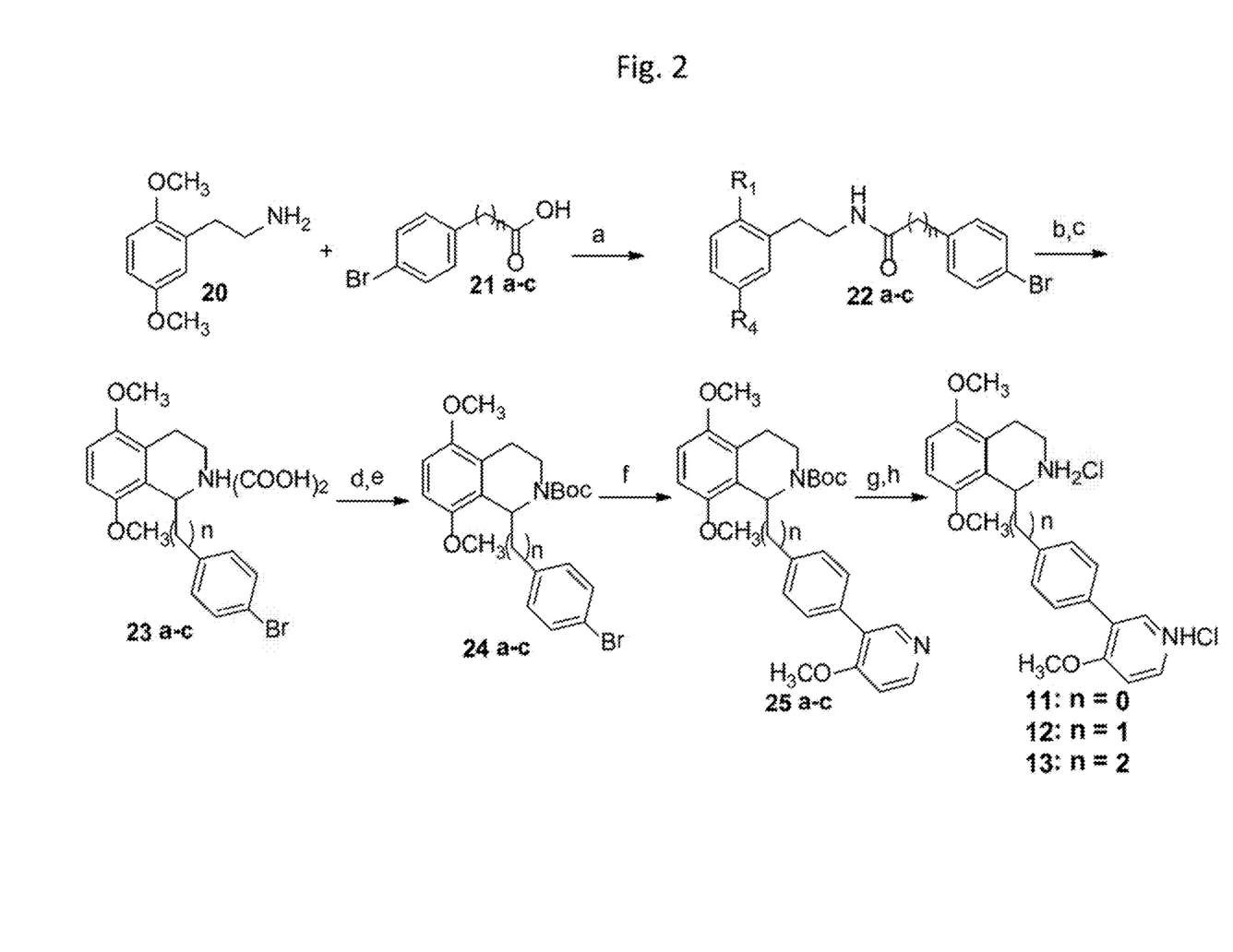
Figure 3:
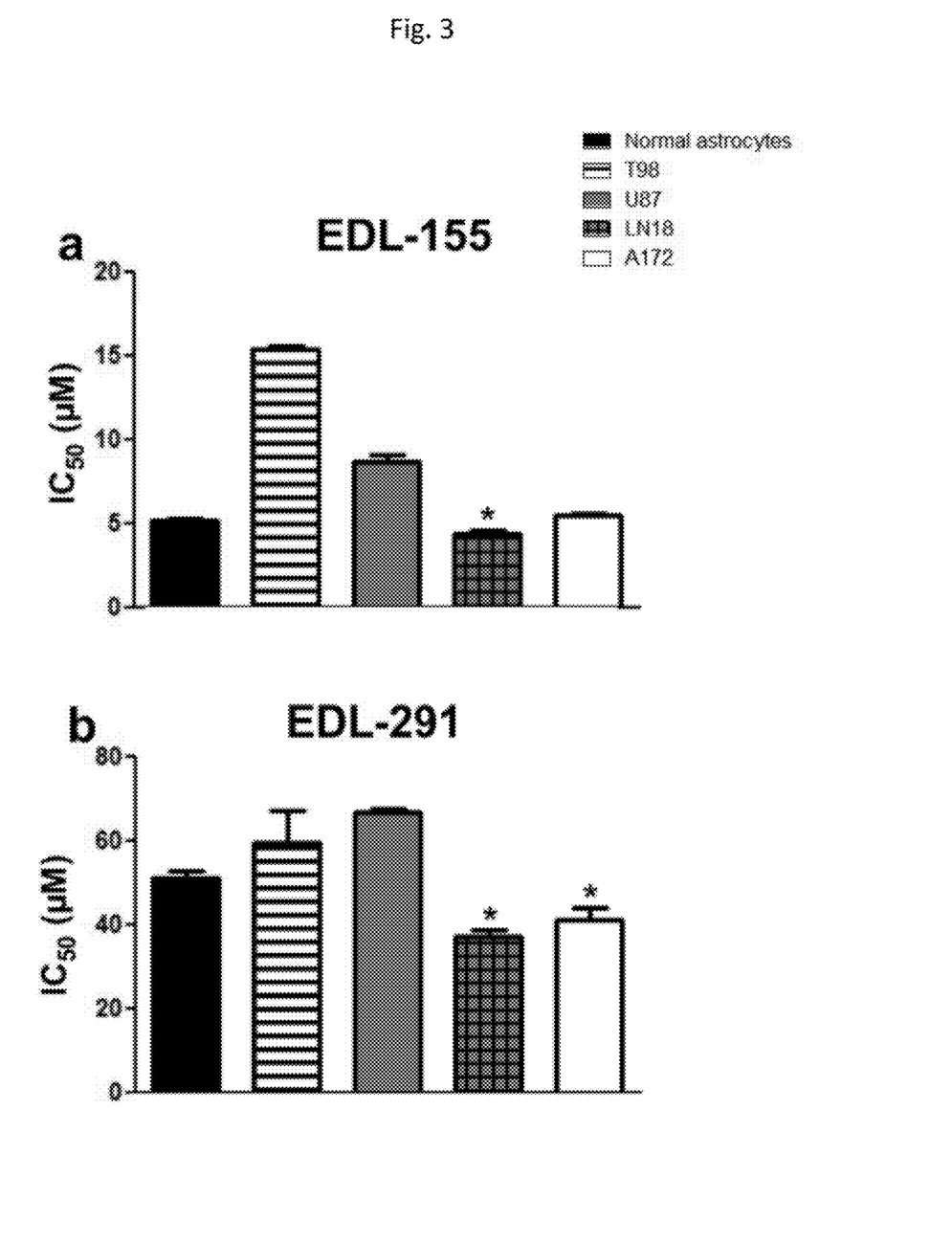
FIG. 3 shows a series of graphs illustrating the inhibitory concentrations determined experimentally for each of the indicated compounds, when applied to the indicated cell types: normal astrocytes, T98, U87, LN18, and A172.

The synthesis of 1,2,3,4-THI derivatives, compounds 9-10 and 11-13 is depicted in Schemes 1 and 2, respectively. The formation of amide derivative (16a) was accomplished by the reaction of 4-bromophenylacetic acid (15) and corresponding amine (14a) in presence of diethylcyanophosphonate, and triethyl amine in quantitative yield. The amide (16a) was subjected to the Bischler-Napieralski cyclization using POCl3 in anhydrous acetonitrile followed by reduction with NaBH4 to obtain the free amine, which was then treated with oxalic acid in MeOH to afford the oxalyl salt (17a). The oxalyl salt (17a) was treated with 1 N NaOH in DCM, and the resulting free amine was allowed to react with di-tert-butyl-dicarbonate to give N-Boc-1,2,3,4-tetrahydroisoquinoline derivative (18a). Compound 18b was prepared by the reported procedure. [17] Compound 18a-b was coupled with 4-methoxypyridine-3-yl-boronic acid in the presence of Pd2(dba)3/XPhos [18] using Suzuki-Miyaura reaction conditions [19-22] to provide compound 19a-b. Deprotection of compound 19a-b using trifluoroacetic acid in DCM followed by acid/base extractions to give free amine, which was then treated with 2M HCl in diethyl ether to produce the desired hydrochloride salts, compounds 9 and 10 in good yield (Scheme 1, FIG. 1).

The final compounds 5,8-dimethoxy-1-(4-(4-methoxypyridin-3-yl)benzyl)-1,2,3,4-tetrahydroisoquinoline dihydrochloride (11), 5,8-dimethoxy-1-(4-(4-methoxypyridin-3-yl) phenethyl)-1,2,3,4-tetrahydroisoquinoline dihydrochloride (12) and 5,8-dimethoxy-1-(3-(4-(4-methoxypyridin-3-yl) phenyl)propyl)-1,2,3,4-tetrahydroisoquinoline dihydrochloride (13) were synthesized similar to the procedure of compound 9 using starting materials 2-(2,5-dimethoxyphenyl) ethanamine (20) and 2-(4-bromophenyl)acetic acid (21a), 3-(4-bromophenyl)propanoic acid (21b) and 4-(4-bromophenyl)butanoic acid (21c) (Scheme 2, FIG. 2).

The synthesized THI analogs were screened for their efficacy against established human glioma cell lines using the MTT colorimetric assay. This assay measures cell viability by quantitating purple formazan crystal formation caused by the reduction of tetrazolium salts in metabolically active cells. The inventors performed a series of experiments to determine the best concentration range for each compound to generate a half-maximal inhibitory concentration (IC50). The IC50 value for each compound represents the mean of triplicate experiments. Primary astrocytes established from the cortices of normal mouse pups were used as the model system to represent the degree of toxicity that would be expected in normal astrocytes in the human brain. The glioma cells and normal astrocytes were exposed to escalating concentrations of each THI compound for five days and then subjected to the MTT assay. Cell viability data at each concentration was used to calculate IC50 values. Results are shown in Table 1.

TABLE 1

Efficacy of analogs against Glioma cells.

| THI Analogs | Mean $IC_{50}$ ± SD (μM) | | | | |
|---|---|---|---|---|---|
| | T98G | U87 | LN18 | A172 | Normal astrocytes[§] |
| EDL-155 (8) | 15.4 ± 0.18 | 8.61 ± 0.46 | 4.32* ± 0.19 | 5.50 ± 0.12 | 5.2 ± 0.06 |
| EDL-291 (9) | 59.5 ± 7.61 | 66.5 ± 1.12 | 37* ± 1.74 | 41.2* ± 2.57 | 51.1 ± 1.38 |
| EDL-355 (10) | 11.78 ± 0.98 | 12.51 ± 1.81 | 7.3* ± 0.83 | 8.99 ± 0.69 | 10.3 ± 2.04 |

TABLE 1-continued

Efficacy of analogs against Glioma cells.

| | Mean IC$_{50}$ ± SD (μM) | | | | |
|---|---|---|---|---|---|
| THI Analogs | T98G | U87 | LN18 | A172 | Normal astrocytes§ |
| EDL-358 (11) | 13.8* ± 0.65 | 16.2* ± 0.65 | 13.7* ± 1.04 | 8.25* ± 0.42 | 24.6 ± 0.79 |
| EDL-360 (12) | 10.38* ± 0.17 | 8.4* ± 0.064 | 5.42* ± 0.06 | 5.6* ± 0.15 | 19.72 ± 2.44 |
| EDL-361 (13) | 14.76 ± 0.68 | 10.46* ± 0.11 | 11.7 ± 0.17 | 15.2 ± 0.98 | 11.92 ± 0.56 |
| TMZ^ | 571 ± 50.42 | 49.1 ± 5.15 | 391.5 ± 77.22 | 65.3 ± 11.97 | >1000 |

§primary astrocyte cultures established from normal mouse brains were used as a model system for normal human astrocytes.
*IC$_{50}$ values were significantly lower in the respective human glioma cell line compared to normal mouse astrocytes (p < 0.05).
^statistical comparisons of IC$_{50}$ values between normal astrocytes and glioma cell lines could not be performed because a IC$_{50}$ could not be calculated in normal astrocytes for TMZ.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A compound of Formula I

(I)

wherein $R^1$, $R^2$, $R^3$, and $R^4$ are each independently H, OH, or OCH$_3$;
$R^5$ is H, Cl, CH$_3$, or COOC(CH$_3$)$_3$;
X is N,
$R^6$ is H or Cl; and
$R^7$ is H or OCH$_3$.

2. The compound as in claim 1 wherein $R^1$ and $R^4$ are H; $R^2$ and $R^3$ are OH; X is N; $R^6$ is H; and $R^7$ is H.

3. The compound as in claim 1 wherein when any two of $R^1$, $R^2$, $R^3$, and $R^4$ are OCH$_3$ and the remaining two of $R^1$, $R^2$, $R^3$, and $R^4$ are H, X is N, $R^6$ is Cl, and $R^7$ is OCH$_3$.

4. A method for treating glioma, the method comprising administering to a subject a therapeutically effective amount of a compound as in formula (I)

(I)

wherein $R^1$, $R^2$, $R^3$, and $R^4$ are each independently H, OH, or OCH$_3$;
$R^5$ is H, Cl, CH$_3$, or COOC(CH$_3$)$_3$;
X is N,
$R^6$ is H or Cl; and
$R^7$ is H or OCH$_3$.

5. The method of claim 4, wherein $R^1$ and $R^4$ are H; $R^2$ and $R^3$ are OH; X is N; $R^6$ is H; and $R^7$ is H.

6. The method of claim 4, wherein when any two of $R^1$, $R^2$, $R^3$, and $R^4$ are OCH$_3$ and the remaining two of $R^1$, $R^2$, $R^3$, and $R^4$ are H, X is N, $R^6$ is Cl, and $R^7$ is OCH3.

7. The method of claim 4, wherein the subject is a human.

8. A pharmaceutical composition comprising a pharmaceutically acceptable carrier and a compound according to claim 1.

* * * * *